United States Patent
Tamaki et al.

[11] Patent Number: 5,949,843
[45] Date of Patent: Sep. 7, 1999

[54] X-RAY TOMOGRAPHY APPARATUS

[75] Inventors: Ryuji Tamaki; Koichi Hirokawa, both of Kashiwa, Japan

[73] Assignee: Hitachi Medical Corporation, Tokyo, Japan

[21] Appl. No.: 08/956,153

[22] Filed: Oct. 22, 1997

[30] Foreign Application Priority Data

Oct. 23, 1996 [JP] Japan .................................. 8-280880

[51] Int. Cl.⁶ .................................................. A61B 6/03
[52] U.S. Cl. ................................. 378/17; 378/19; 378/901
[58] Field of Search ................................. 378/15, 17, 19, 378/901

[56] References Cited

U.S. PATENT DOCUMENTS 5,668,846  9/1997  Fox et al. .................................... 378/4

FOREIGN PATENT DOCUMENTS 4-227238  8/1992  Japan .

Primary Examiner—David Vernon Bruce
Attorney, Agent, or Firm—Antonelli, Terry, Stout & Kraus, LLP

[57] ABSTRACT

An X-ray computer tomography apparatus equipped with an X-ray scanner for converting X-rays emitted from an X-ray source to a fan beam by a collimator, irradiating the fan beam to an object and detecting the X-rays passing through the object of a multi-channel X-ray detector includes a memory for storing data of a change quantity of a fan beam position with respect to a tilt angle of the X-ray scanner, a device for setting the X-ray scanner to a predetermined tilt angle, a control unit for controlling the position of the X-ray source so that the fan beam position becomes a reference position, on the basis of the change quantity of the fan beam position corresponding to the predetermined tilt angle read out from the memory and set, and a unit for executing X-ray tomography measurement or imaging of the object under the state where the fan beam position is controlled to the reference position.

6 Claims, 4 Drawing Sheets

X-RAY TOMOGRAPHY APPARATUS

BACKGROUND OF THE INVENTION

This invention relates to an X-ray computer tomography (CT) apparatus having a changing mechanism of a tilt angle of an X-ray scanner.

JP-A-4-227238 as a laid-open publication of a Japanese patent application discloses a prior art example for correcting an error of an X-ray fan beam position. This prior art example teaches to correct the error of the X-ray fan beam position in a detector mechanism resulting from a mal-arrangement of the position of a focal point spot of an X-ray tube. In the first concrete example, the movement of an irradiation area of the X-ray fan beam resulting from the mal-arrangement of the focal spot of the X-ray tube (movement in a slice width direction) is detected by a Z-axis offset detector (when a coordinates system set in the slice width direction is defined as the Z axis) and position control of a collimator is effected in such a manner as to eliminate this offset. In the second concrete example, mechanical deflection or a thermal drift of the focal spot of the X-ray is calculated by using an anticipation model and position control of the collimator is effected so as to correct the spot position fluctuation of the X-ray tube obtained by this calculation. The error can be eliminated by correcting the fluctuation of the focal spot of the X-ray tube.

The anticipation model described above includes a thermodynamic/geometric model and a mechanical stress model. The former anticipates the fluctuation of the focal spot of the X-ray tube due to the thermal drift and the latter anticipates the fluctuation of the focal spot of the X-ray tube determined or analyzed empirically by a function of a rotating speed and a tilt angle of an X-ray scanner.

The mechanical stress model of the prior art example described above acquires the fluctuation of the focal spot of the X-ray tube determined or analyzed empirically as a function of the rotating speed and the tilt angle of the X-ray scanner, but a problem remains unsolved in practice in that a correct model is difficult to create.

When, for example, any shake (play) exists at a support portion of a rotating anode of the X-ray tube as an X-ray source, this cannot be easily expressed as a formula manipulation model. Further, when tilt angle control (that is, tilt angle for tilting forward or rearward the X-ray scanner) is conducted, there develops often the case where the X-ray fan beam position does not coincide under the erecting state when the X-ray scanner is returned from the forward tilt position to the erecting state and when it is returned from the rearward tilt state to the erecting state. Nonetheless, the formula manipulation model does not take this discrepancy into account. When tilt angle control of the X-ray scanner is effected, influences of the gravity and the centrifugal force may exist but these influences are not taken into account. For these reasons, a ring artifact is likely to develop in a slice image.

SUMMARY OF THE INVENTION

The present invention provides an X-ray CT apparatus which can reliably correct the fluctuation of the X-ray fan beam position occurring in practice.

The present invention provides an X-ray CT apparatus having an X-ray scanner including an X-ray source, a collimator for converting X-rays from the X-ray source to a fan beam and a multi-channel X-ray detector so disposed as to oppose the X-ray source and the collimator through a measurement space of an object, and capable of changing a tilt angle of the X-ray scanner, and this X-ray CT apparatus comprises a memory for storing data of a change quantity of a fan beam position with respect to each tilt angle; means for setting the X-ray scanner to a predetermined tilt angle; means for reading the change quantity of the fan beam position corresponding to the set tilt angle from the memory and executing position control of the X-ray source so that the fan beam position becomes a reference fan beam position; and means for setting the fan beam position to the reference fan beam position and then executing X-ray CT measurement or imaging of the object.

Further, the present invention provides an X-ray CT apparatus having an X-ray scanner including an X-ray source, a collimator for converting X-rays from the X-ray source to a fan beam and a multi-channel detector so disposed as to oppose the X-ray source and the collimator through a measurement space of an object, and capable of changing a rotating speed of the X-ray scanner, and this X-ray CT apparatus comprises a memory for storing data of a change quantity of a fan beam position with respect to a rotating speed value; means for setting the X-ray scanner to a predetermined rotating speed; means for reading out a change quantity of a fan beam position corresponding to a set rotating speed from the memory and executing position control of the collimator so that the fan beam position becomes a reference fan beam position; and means for setting the fan beam position to the reference fan position and then executing X-ray CT measurement or imaging of the object.

DESCRIPTION OF THE PREFERRED EMBODIMENTS

Figure 1:
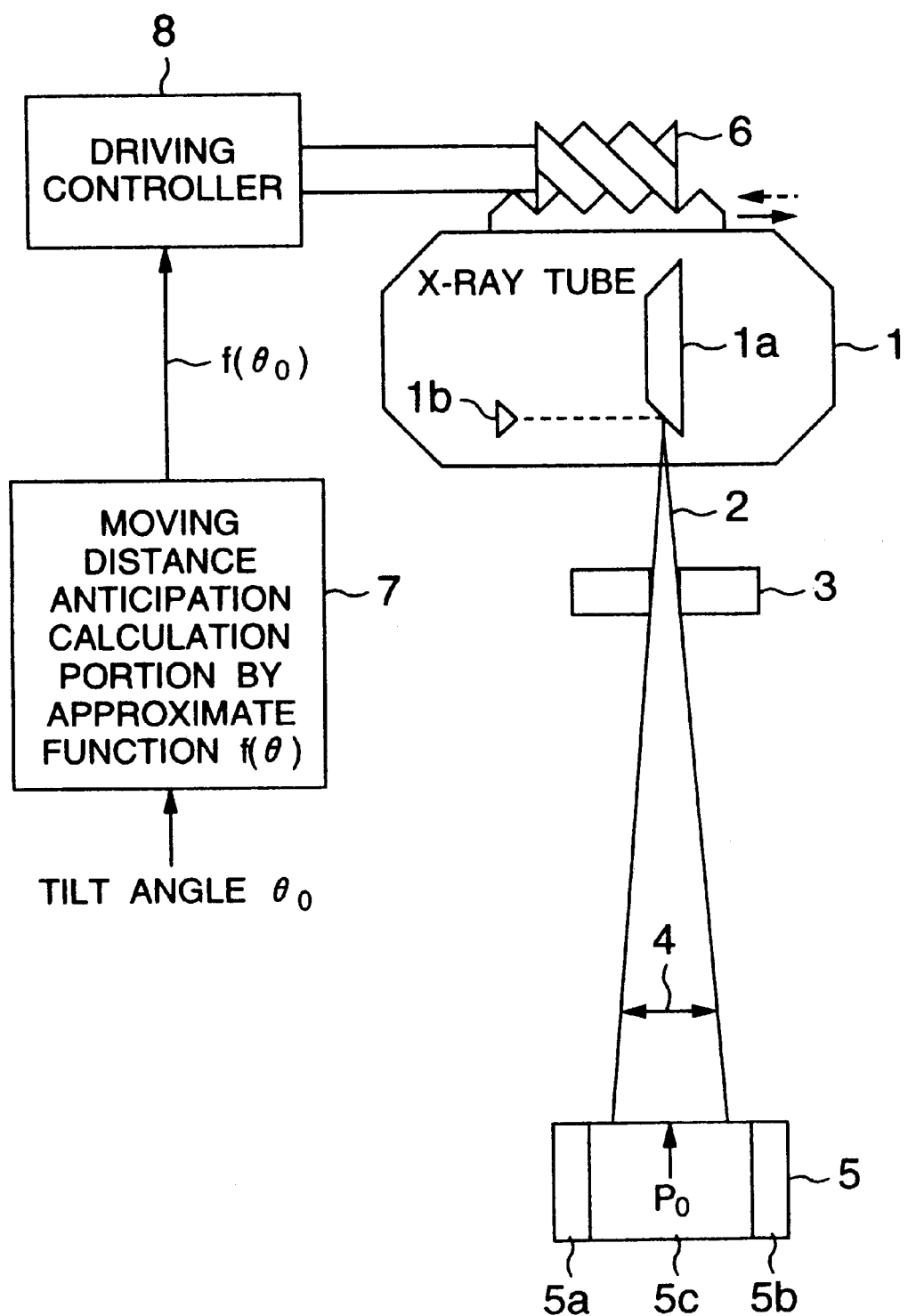
FIG. 1 is a block diagram showing an X-ray CT apparatus according to one embodiment of the present invention.

FIG. 1 shows an X-ray CT apparatus for executing X-ray source position control according to one embodiment of the present invention. An X-ray tube 1 as an X-ray source includes therein a rotary anode 1a and a filament 1b and is allowed to move its position in a direction represented by arrows of solid line or a direction represented by arrows of dotted line by a driving mechanism 6. The direction of the solid line or the dotted line is a slice width direction but is not a direction extending in a beam plane of a fan beam. Here, the slice width direction and the beam plane of the fan beam orthogonally cross each other.

A collimator 3 is employed so as to convert the beams to the fan beam. A multi-channel detector 5 is so disposed as to oppose the X-ray tube 1 while interposing a measurement space between them, and rotates round the measurement space under this opposing state. The X-ray tube 1, the collimator 3 and the multi-channel detector 5 are mounted into a rotary member referred to as an "X-ray scanner".

Referring to FIG. 1, the multi-channel detector 5 represents only one channel and other channels are disposed in the depth-wise direction of the sheet of the drawing in a multi-channel configuration. Right and left end portions 5a and 5b are insensitive areas while a center 5c is a sensitive area. In FIG. 1, a center position $P_0$ of the detector is a reference fan beam position. The phenomenon in which the center of the slice width 4 of the X-ray beam moves to the right and left is defined as the "shift" of the fan beam position to the right and left. Since this transverse shift is not desirable, it is necessary to detect whether or not this shift exists, then to execute position control of the X-ray tube 1 by a distance corresponding to the shift in the opposite direction if any shift exists, and to locate always the center of the slice width 4 of the X-ray beam 2 to the reference fan beam position $P_0$.

Figure 2:
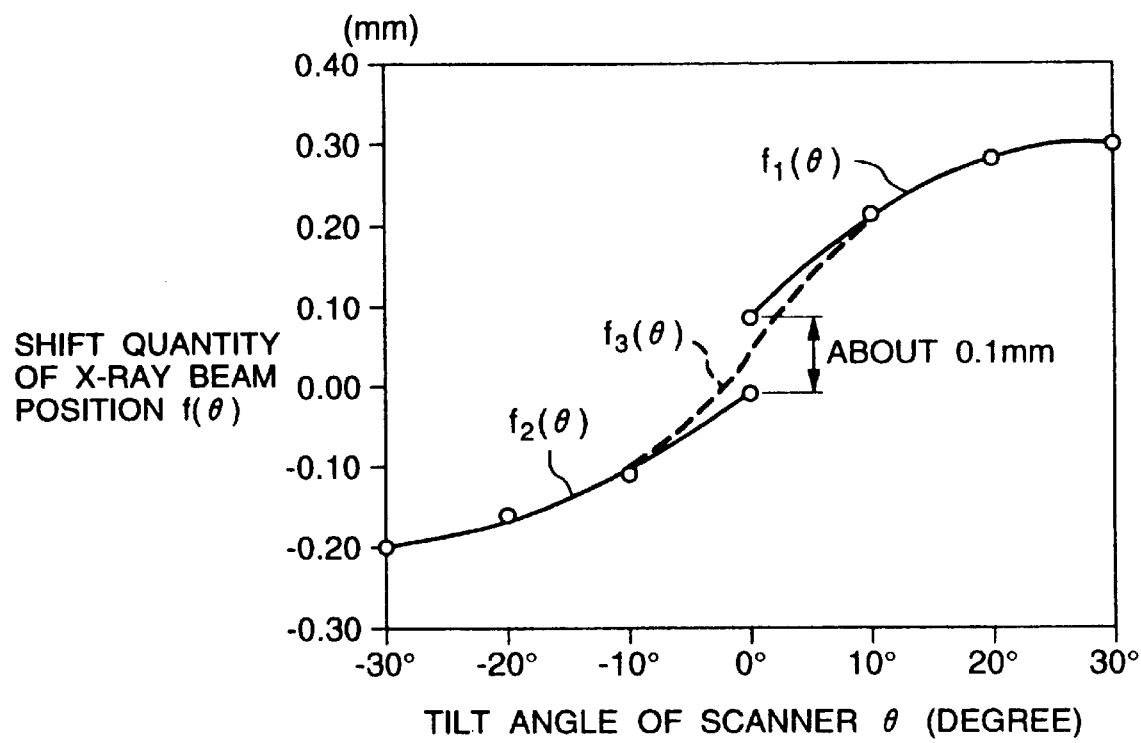
FIG. 2 is a diagram showing a measurement result of a tilt angle of an X-ray scanner and an X-ray beam shift quantity.

An anticipation calculation portion 7 and a driving controller 8 are means for controlling the driving mechanism 6. The anticipation calculation portion 7 includes a memory for storing a measurement data of title angle θ-vs.-shift quantity f(θ) of the X-ray fan beam position. This measurement is executed in advance to acquire necessary data. In other words, the shift quantity F(θ) of the X-ray fan beam position is measured every time by variously changing the tilt angle θ of the X-ray scanner before the CT measurement and imaging are carried out. FIG. 2 shows the measurement shift quantity f(θ) at each angle of θ=30°→20°→10°→0° when the scanner is returned from a forward tilt state to an erecting state (0°) and at each tilt angle of θ=−30°→−20°→−10°→0° when the scanner is returned from a rearward tilt state to the erecting state (0°). In this way, the measurement data is stored in the memory by associating the tilt angle θ with the shift quantity f(θ). Incidentally, a difference of about 0.1 mm exists at θ=0° in the shift quantity between the shift from the forward tilt to the erecting state and the shift from the rearward tilt to the erecting state.

Setting of the tilt angle θ is made either continuously or discretely by a value smaller than the 10-degree unit described above. The anticipation calculation portion 7 reads out the content of this memory and calculates the shift quantities at other tilt angles θ by an approximate function. FIG. 2 shows $f_1(θ)$, $f_2(θ)$ and $f_3(θ)$ as an example of the approximate function, where $f_1(θ)$ represents the approximate function in the case of the shift from the forward tilt to the erecting state, $f_2(θ)$ does the shift from the rearward tilt to the erecting state and $f_3(θ)$ does an approximate function for making discontinuity of the shift quantities of the forward and rearward tilts continuous. In either case, approximation is made by a curve connecting the measurement shift quantity f(θ).

These approximate functions, too, are calculated before the CT measurement and imaging and are stored in the memory of the anticipation calculation portion 7. The tilt angle θ is decided at the time of the CT measurement and imaging, and tilt control of the X-ray scanner is effected so as to attain the tilt angle $θ_0$ so decided. The tilt angle $θ_0$ is inputted to the anticipation calculation portion 7, and the X-ray fan beam shift quantity $f(θ_0)$, which is calculated in advance, is read out from the memory. The driving controller 8 inputs the shift quantity $f(θ_0)$ and controls the driving mechanism 6 in such a fashion that the fan beam position $f(θ_0)$ at that time reaches the reference fan beam position $P_0$.

Figure 3:
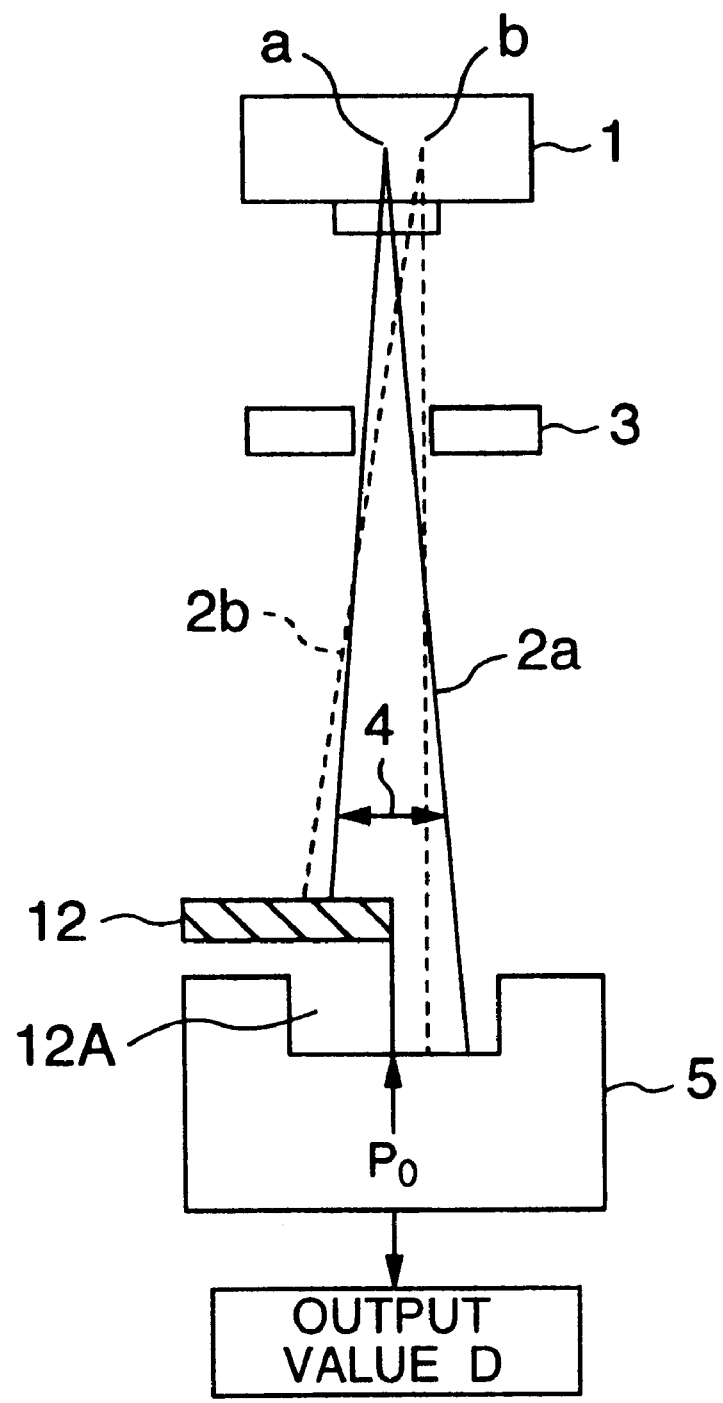
FIG. 3 is a perspective view of a system for detecting the X-ray beam shift.

FIG. 3 shows a measurement system for determining the X-ray fan beam position (shift quantity) f(θ) with respect to the tilt angle θ shown in FIG. 2. An X-ray shield plate 12 is positioned on the fan beam input side of the channel device for measuring the shift quantity on the multi-channel detector 5 so that a shield end portion 12A thereof reaches the center reference position $P_0$. When the shift does not exist in the sensitive area of the channel device, the X-ray input corresponding to the half of the slice width exists but when the shift is left shift, its quantity becomes small and when it is the right shift, the quantity becomes great. Therefore, the shift quantity and its direction can be known from the degree of the output quantity of the channel device. In this way, when the focal point of the X-ray tube 1 moves a→b, the X-ray beam, too, shifts to 2a–2b and the slice center position shifts in the corresponding way. When the shift occurs, the X-ray quantity shielded by the X-ray shield plate 12 changes in the corresponding way, too. Therefore, the shift quantity can be detected by monitoring the output D of the detection device.

Figure 4:
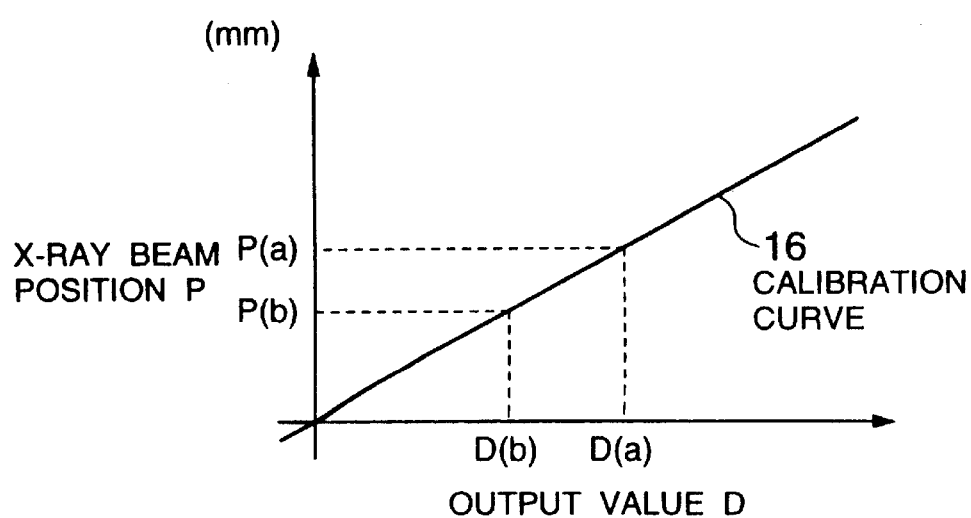
FIG. 4 is a graph showing a measurement result of an X-ray detection device and an X-ray beam position.

FIG. 4 shows the relation (calibration curve 16) between the output value D of the detection device and the X-ray beam position P. The X-ray beam position corresponding to the output value can be calculated by determining in advance this relation. Assuming that D(a) is the reference position $P_0$ in FIG. 4, P(a)–P(b) is the original shift quantity f(θ). Position control of the X-ray tube 1 is carried out so as to eliminate this shift quantity.

FIG. 4 shows an example at a certain tilt angle. The tilt angle is changed by 10 degrees for both forward and rearward tilts and measurement is executed eight times in total by using the measurement system shown in FIG. 3. The measurement procedure advances towards the erecting state as listed below:

θ=−30°→−20°→−10°→0°

θ=+30°→+20°→+10°→0°

The plotted points of white circle (○) in FIG. 2 represent the measurement result.

Next, two approximation methods will be explained.
(1) Approximation is made to the second-order (or third or more order) function by the method of least squares separately for the forward tilt and the rearward tilt in consideration of discontinuity resulting from any shake at the support portion of the rotary anode of the X-ray tube. Solid lines in FIG. 2 represent $f_1(t)$, $f_2(t)$ and $f_3(t)$ obtained in this way.

In the case of the discontinuous point θ=0° in anticipation calculation, the calculation is made dividedly for the following cases on the basis of the history of the tilt angle.

(a) When θ is set to 0° from the forward tilt state, θ=0° is inputted to the approximate function $f_1(θ)$ on the forward tilt side.

(b) When θ is set to 0° from the rearward tilt state, θ=0° is inputted to the approximate function $f_2(θ)$ on the rearward tilt side.

(c) When the erecting state is kept, the shift of the X-ray beam is regarded as nil.
(2) Approximation is made by the function of third or higher order $f_3(θ)$ inclusive of the discontinuous portion resulting from the shake. In this case, division of the cases such as (1) is not necessary. However, when the shake is great, accuracy drops at the discontinuous portion.

The method of the position control of the X-ray tube 1 will be explained.
(1) The X-ray beam position P and the shift quantity f(θ) are the values on only the X-ray detector and strictly speaking, they are not the position itself of the X-ray tube 1. To execute stricter position control, therefore, the correspondence relation between the shift quantity f(θ) of the X-ray beam and the position f'(θ) of the X-ray tube 1 is determined and stored in advance in the memory inside the controller 8, the position of the X-ray tube 1 is controlled by utilizing the output of this memory so that the beam center position reaches the reference position $P_0$. Incidentally, if the shift quantity and the position of the X-ray tube 1 have a linear relation, only the tilt quantity may be calculated (no calibration is necessary in the case of a straight line of 45°). Alternatively, the calibration line 16 is set afresh by substituting the X-ray beam position P for the position Q of the X-ray tube.

(2) The item (1) represents the example of the open control, and there is another method which controls the X-ray tube 1 so as to attain the reference position $P_0$ by closed control, that is, by feedback control. This method utilizes the measurement system shown in FIG. 3 and negatively feeds back the output value D to the driving controller 8 so that the output value D reaches the output value $D_0$ at the reference position $P_0$.

Figure 5:
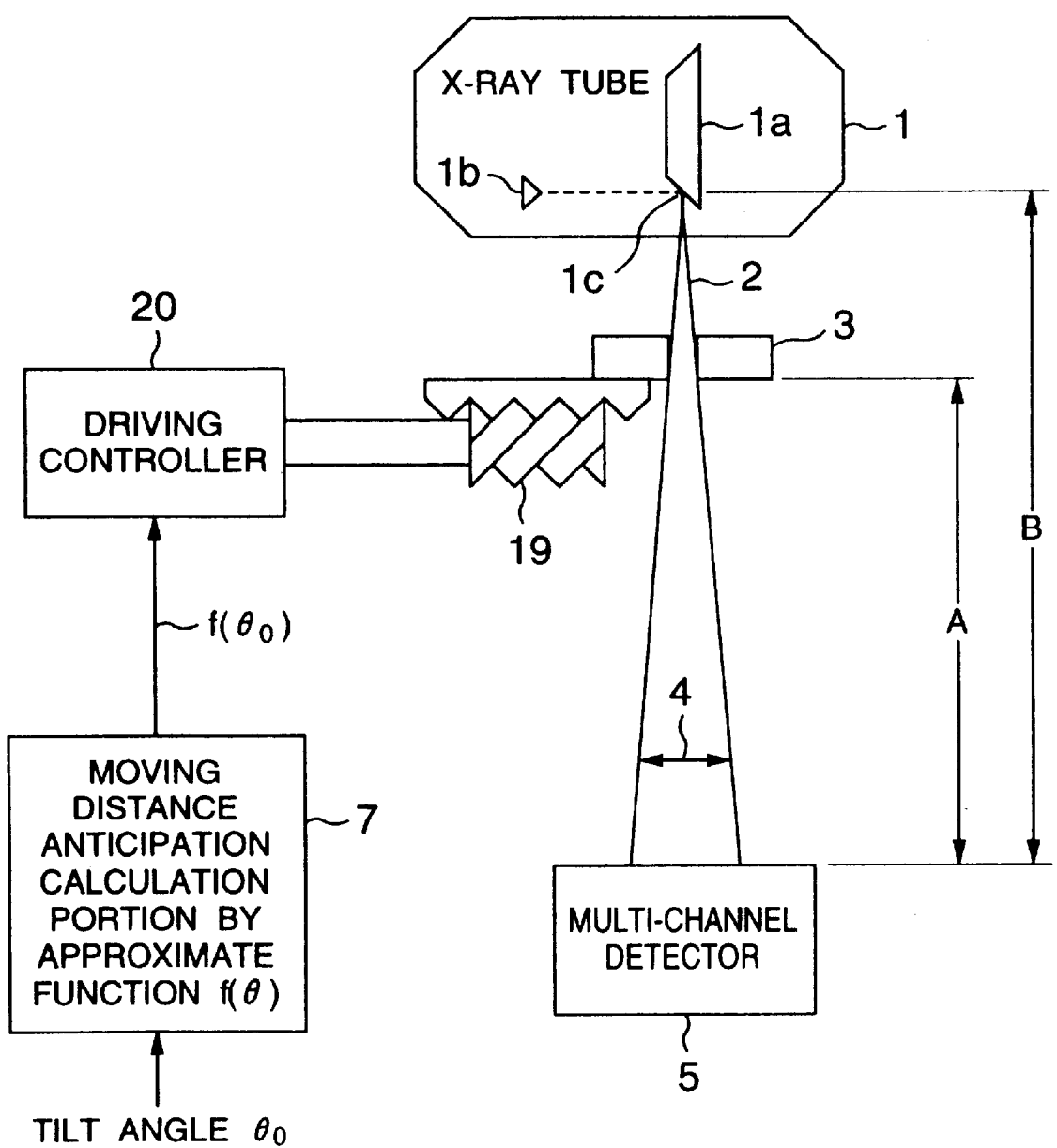
FIG. 5 is a block diagram showing an X-ray CT apparatus according to another embodiment of the present invention.

FIG. 5 shows another embodiment for executing collimator position control instead of the X-ray tube. A driving mechanism 19 is disposed so as to execute position control of the collimator 3 in the slice direction. Furthermore, a driving controller 20 is disposed to control this driving mechanism 19. However, whereas detection of the shift quantity is made by the detection device 5 and is handled as the shift quantity of the X-ray tube position in the foregoing embodiment, position control in FIG. 5 is made by the collimator 3 interposed between the X-ray tube 1 and the detection device 5 and for this reason, position calibration for converting to the collimator position is necessary. Therefore, the calibration value $g(\theta)$ is determined by the following equation for the function $f(\theta)$ (inclusive of the approximate functions $f_1(\theta)$ to $f_3(\theta)$, or $f'(\theta)$):

$$g(\theta) = f(\theta) \cdot (A/B)$$

Here, A represents the distance between the detection device 5 and the collimator 3, and B does the distance between the detection device 5 and the focal point 1c of the X-ray tube. The calibration calculation described above is conducted inside the driving controller 20 (or in the calculation portion 9) and control is executed by using this calibration value $g(\theta)$ so as to control the driving mechanism 19, to eliminate the shift quantity and to attain the reference position P.

The driving mechanisms 6 and 19 described above are directed to the movement in the slice width direction, but when they can drive in the directions orthogonally crossing the slice width direction (both two axes), correction of the beam position as well as the movement control in the directions other than the slice width direction become possible.

The shift inspection can be carried out by a shift inspection method described in JP-A-4-227238 in place of the X-ray shield plate 12 shown in FIG. 3, and the structure of the collimator, too, may be the similar to the one described in JP-A-4-227238.

The shift occurs in some cases depending on the rotating speed of the X-ray scanner besides the tilt angle. In such a case, shift correction can be executed similarly by measuring in advance the shift quantity by using the rotating speed as a parameter, and the processing becomes easier and simpler by determining an integrated shift quantity by using both of the tilt angle and the rotating speed as the parameters.

The present invention can correct the shift of the X-ray beam position in tilt measurement and can reduce or eliminate the ring artifact appearing in the slice image (reconstructed image).

Because the approximate function $f(\theta)$ is determined for an individual X-ray CT apparatus, the X-ray tube can be used without specifically considering the shake of the X-ray tube.

The functions of the anticipation calculation portion 7 for the moving distance of the beam explained in the foregoing embodiments can be accomplished by a computer including a CPU, a memory storing an anticipation calculation program and measurement data and a signal I/O interface.

What is claimed is:

1. An X-ray CT apparatus having an X-ray scanner including an X-ray source, a collimator for converting X-rays from said X-ray source to a fan beam and a multi-channel X-ray detector so disposed as to oppose said X-ray source and said collimator through a measurement space of an object, and capable of changing a tilt angle of said X-ray scanner, said X-ray CT apparatus comprising:

a memory for storing data of a change quantity of a fan beam position with respect to each tilt angle;

means for setting said X-ray scanner to a predetermined tilt angle;

means for reading the change quantity of the fan beam position corresponding to the set tilt angle from said memory and executing position control of said X-ray source so that the fan beam position becomes a reference fan beam position; and means for setting the fan beam position to the reference fan beam position and then executing tomography measurement or imaging of said object.

2. An X-ray CT apparatus according to claim 1, wherein said memory stores data expressing the change quantities of the fan beam positions corresponding to different tilt angles by a combination of a plurality of approximate curve functions.

3. An X-ray CT apparatus according to claim 1, wherein a control unit controls the position of said X-ray source so that a practical detection value by said multi-channel X-ray detector becomes a reference detection value when said fan beam exists at said reference position.

4. An X-ray CT apparatus having an X-ray scanner including an X-ray source, a collimator for converting X-rays from said X-ray source to a fan beam and a multi-channel detector so disposed as to oppose said X-ray source and said collimator through a measurement space of an object, and capable of changing a rotating speed of said X-ray scanner, said X-ray CT apparatus comprising:

a memory for storing data of a change quantity of a fan beam position with respect to a rotating speed value;

means for setting said X-ray scanner to a predetermined rotating speed;

means for reading out a change quantity of a fan beam position corresponding to a set rotating speed from said memory and executing position control of said collimator so that said fan beam position becomes a reference fan beam position; and means for setting said fan beam position to said reference fan position and then executing X-ray CT measurement or imaging of said object.

5. An X-ray CT apparatus according to claim 4, wherein said memory stores data representing the change quantities of said fan beam positions corresponding to different rotating speed values by a combination of a plurality of approximate curve functions.

6. An X-ray CT apparatus according to claim 4, wherein a control unit controls the position of said collimator so that a practical detection value by said multi-channel X-ray detector becomes a reference detection value when said fan beam exists at said reference position.

\* \* \* \* \*